United States Patent [19]

Murtha et al.

[11] 4,122,125

[45] Oct. 24, 1978

[54] HYDROALKYLATION USING MULTIMETALLIC ZEOLITE CATALYST

[75] Inventors: Timothy P. Murtha; William A. Jones; Ernest A. Zuech; Marvin M. Johnson, all of Bartlesville, Okla.

[73] Assignee: Phillips Petroleum Company, Bartlesville, Okla.

[21] Appl. No.: 739,766

[22] Filed: Nov. 8, 1976

[51] Int. Cl.$^2$ ............................................. C07C 15/00
[52] U.S. Cl. ............................ 260/668 R; 252/455 Z; 260/668 B
[58] Field of Search ....................... 260/668 R, 668 B; 252/455 Z

[56] References Cited

U.S. PATENT DOCUMENTS

| 3,829,515 | 8/1974 | Zuech et al. | 260/668 R |
| 3,839,477 | 10/1974 | Suggitt et al. | 260/668 R |

*Primary Examiner*—Veronica O'Keefe

[57] ABSTRACT

An aromatic hydrocarbon is contacted under hydroalkylation conditions and in the presence of hydrogen with a catalyst comprising at least one ruthenium compound and at least one nickel compound supported on a calcined, acidic, rare earth-treated crystalline zeolite.

12 Claims, No Drawings

HYDROALKYLATION USING MULTIMETALLIC ZEOLITE CATALYST

The invention relates to a hydroalkylation process, a composition useful as a catalyst in said process and a method for producing said composition.

Prior art catalysts in the field of hydroalkylation processes suffered from several drawbacks. These deficiencies of the prior art catalysts for the hydroalkylation reaction included: (1) Many prior art compositions useful as catalysts show a rather low productivity as judged by the low liquid hourly space velocities (LHSV) that are utilized in the prior art. Thus a more active and more selective hydroalkylation catalyst is desired. (2) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus it is desirable that a more simplified and less expensive process for making active and selective catalysts be found. (3) Certain catalysts of the prior art for the hydroalkylation reaction were of fixed acidity because of the type of support material utilized. This left little variation that could be made in this important property of the hydroalkylation catalyst. It is, therefore, desirable that catalysts be developed which are varied easily in their acidity characteristics.

It is an object of the present invention to hydroalkylate aromatic compounds.

Another object of the present invention is to provide a method for producing a hydroalkylation catalyst.

Another object of the invention is a composition useful as a catalyst in hydroalkylation reactions which is more active and more selective than prior art catalysts.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a catalyst comprising at least one ruthenium compound and at least one nickel compound supported on a calcined, acidic, rare earth-treated crystalline zeolite. Such a catalyst is a highly active and selective catalyst.

Further according to the invention, a composition comprises at least one ruthenium compound and at least one nickel compound supported on a calcined, acidic, rare earth-treated crystalline zeolite.

Further according to the invention, the above composition is prepared by contacting a crystalline zeolite with an aqueous cation exchange solution comprising at least one rare earth compound and at least one ammonium compound; removing the zeolite from said solution and washing said zeolite with water to remove excess ions; calcining said zeolite; cooling said calcined zeolite; impregnating said calcined zeolite with a solution comprising at least one ruthenium compound and at least one nickel compound in a suitable solvent; and removing said solvent by evaporation. The acidity of the above composition is easily adjusted by varying the conditions under which the cation exchange step is carried out.

DETAILED DESCRIPTION OF THE INVENTION

Based on the above description and disclosure, the composition of the instant invention can be briefly described as a Type X or Type Y crystalline zeolite which has been cation exchanged with rare earth and ammonium compounds followed by a calcination step and said calcined support then impregnated with ruthenium and nickel compounds to give the final composition. Although not absolutely necessary, it is preferred because of improved results that the above catalyst be treated with hydrogen prior to introduction of the aromatic hydrocarbon feed in the hydroalkylation process.

The compositions of the instant invention are useful as catalysts and to some extent solve or obviate each of the above-mentioned deficiencies of the prior art catalyst. For example, the compositions of the invention when used as a catalyst appear to operate at higher levels of productivity in that they show a higher degree of activity and selectivity than certain of the prior art catalysts; the process of making the compositions of the instant invention is simple and straightforward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth and ammonium compounds such that the cation metal content of the support is partially exchanged. Generally the cationic metal is an alkali metal which is removed by cation exchange such that the alkali metal content ranges from about 0.01 to about 2 percent by weight; however, the runs carried out in accordance with the invention and reported herein indicate that good results can be obtained employing an alkali metal content ranging from about 0.1 to about 1 percent by weight. The more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK40 (Type Y) and 13X (Type X) from the Linde Division of Union Carbide Corporation.

The alkali metal form of the crystalline zeolites usually comprises sodium as the alkali metal and said zeolites are treated under cation exchange conditions with a mixture of rare earth and ammonium compounds in accordance with the present invention in order to provide a suitable support material for use in the preparation of the compositions of the invention.

It is contemplated that any of the readily available rare earth metal compounds may be employed. Generally, the compounds used are those in which the rare earth metal-containing ion is present in the cationic state. Representative rare earth metal compounds include nitrates, bromides, acetates, chlorides, iodides and sulfates of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly; however, it is often convenient to employ mixtures of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

As noted above, the zeolite material is cation exchanged with a mixture comprising at least one rare earth compound and at least one ammonium compound according to the instant invention. Any convenient ammonium compound may be employed although the chloride is preferred because it is inexpensive and readily available. The weight ratio of ammonium compound to rare earth compound in the aqueous exchange solution can be selected over a broad range. Generally, the weight ratio of ammonium compound to rare earth compound is within the range of from about 0.05:1 to about 20:1, although the data contained herein indicates that a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite is within the ranges specified below. Broadly, the content of the final catalyst composite in terms of the rare earth elements is from about 2 to about 25 weight percent. The runs described herein indicate that the rare earth content of the catalyst can be within the range of from 5 to 20 weight percent. Good results were obtained employing a rare earth content of about 10 percent by weight. As noted above, the alkali metal content, for example sodium, of the exchanged catalyst support is generally from about 0.01 to about 2 percent by weight; however, the runs described herein indicate that good results can be obtained employing an alkali metal content ranging from about 0.1 to about 1 percent by weight.

The procedure whereby the Type X and Type Y zeolites are treated with aqueous solutions of rare earth and ammonium compounds to replace a portion of the alkali metal content of the zeolite is a cation exchange process which can be carried out in a batch or continuous fashion. Generally, the exchange process is carried out on a continuous basis under the following typical conditions. A fixed bed of the zeolite material is treated with said aqueous solution of the rare earth and ammonium compounds at a temperature of 90 to 100° C. under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth cations and ammonium ions in the zeolite. The exchanged zeolite is then washed free of excess ions from the exchange step with water. The excess wash water is removed by drying the zeolite at a temperature ranging from about 100° to about 300° C. and thereafter slowly increasing the temperature to a temperature ranging from about 200° to about 550° C. in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity. The zeolite support thus prepared is now ready for impregnation with ruthenium and nickel compounds in order to prepare the compositions of the instant invention.

The above-described support is then impregnated with a solution of at least one ruthenium compound and at least one nickel compound followed by evaporation of the solvent used in the impregnation step. Evaporation of the solvent can be conducted under vacuum if desired. Suitable solvents include water, alcohols, such as ethanol, ketones, such as acetone, and the like. Various ruthenium and nickel compounds can be employed in the impregnation step, such as the nitrates, acetates, chlorides and the like. Particularly preferred are the chlorides because of cost and availability. It is preferred that the impregnation step be carried out with a mixture of the ruthenium and nickel compounds although the impregnation can be carried out with the separate compounds in either order as long as the desired level of ruthenium and nickel is achieved in the final catalyst composite. The impregnation is generally carried out under what may be called "total impregnation" whereby the entire solids in the solutions used in the impregnation are left on the catalyst support and the liquid solvent for said compounds is simply removed by evaporation.

The ruthenium content and nickel content in the final composition can be selected over a broad range. Generally, the ruthenium content ranges from 0.01 to about 1 percent by weight although the runs described herein indicate that good results can be obtained employing a ruthenium content within the range of from about 0.05 to 0.25 percent by weight. These same ranges also apply for the nickel content of the final product. However, for improved catalytic activity, the nickel:ruthenium weight ratio in the final composite should be in the range of from about 1:1 to about 2:1.

The composition described above is employed for the hydroalkylation of aromatic hydrocarbons to produce cycloalkyl aromatic hydrocarbons. The feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts in general. However, it is believed that a small amount of water, e.g., 10–20 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 690 to about 13,800 kPa (about 100 to about 2,000 psig), the hydrogen feed rate generally ranging from about 0.2 to about 1 mole per mole of aromatic hydrocarbon feedstock per hour, and the reaction temperature generally ranging from about 100° to about 250° C. Based upon the runs described herein good results can be obtained employing a liquid hourly space velocity (LHSV) within the range of from about 5 to about 25, a reaction pressure within the range of from about 1,380 to about 6,900 kPa (about 200 to about 1,000 psig), the hydrogen feed rate within the range of from about 0.2 to about 1 mole per mole of aromatic hydrocarbon feed per hour, and the reaction temperature within the range of from about 140 to about 200° C.

The hydroalkylation reaction is conveniently carried out by having the above-described catalyst in a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions, although a batch process is less preferred because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to pre-reduce the catalyst. Based upon the runs described hereinafter, the hydrogen pressure and feed rate for the pretreating step generally is the same as that to be employed when contacting the aromatic hydrocarbon with the catalyst. In the hydroalkylation steps of the examples hereinafter described, the catalyst in the reactor was first reduced at 150° C. for 15 minutes under 3,450 kPa (500 psig) hydrogen at a hydrogen flow rate of 0.32 liter per minute before benzene was introduced to the reactor. Hydrogen pressure during the hydroalkylation process was maintained at 3,450 kPa (500 psig) and at a flow rate of about 0.32 liter per minute.

EXAMPLE I (Runs 1-2)

A composition outside the scope of this invention in that no rare earth compounds were employed was prepared in the following manner. A glass tube of 45 millimeter diameter which was equipped with an electrical heating means and means for passing liquid through the tube was charged with 200 grams of 150 inch diameter microspheres of Type X crystalline zeolite (Davison 10A mole sieves, Davison Chemical Division of W. R. Grace & Co., Baltimore, Maryland) having a pore diameter of about 10 angstroms. A solution of 100 grams of ammonium chloride in 4 liters of water was pumped over the above bed of crystalline zeolite particles at a temperature of about 95° to 100° C. at a rate of about 100 ml per hour in an upflow arrangement. After the entire solution of ammonium chloride had been passed over the bed of crystalline zeolite particles, the support material was filtered and washed six times with 350 ml portions of water and allowed to dry in ambient air. The support material was then dried carefully under slowly increasing temperature up to 288° C. (550° F.) and held at that temperature for about two hours and then heated slowly up to 594° C. (1100° F.) over two and one-half hours and then for three hours at 594° C. (1100° F.). The support material was then allowed to cool to 288° C. (550° F.) and held at this temperature for about twenty-four hours. The material was removed from the furnace and allowed to cool in ambient air to recover 166.4 grams of the treated support material. Analysis demonstrated that this support material contained 3.98 weight percent sodium.

Twenty grams of the crystalline zeolite which had been treated with ammonium chloride and then calcined as described above was treated with a solution of 0.0494 gram of ruthenium chloride ($RuCl_3$) and 0.0841 gram of nickel chloride hexahydrate ($NiCl_2 \cdot 6H_2O$) in about 80 ml of absolute ethanol. The absolute ethanol was removed under reduced pressure on a rotary evaporator. This catalyst thus prepared contained 0.10 percent by weight ruthenium and 0.10 percent nickel.

The catalyst described above which does not contain rare earths according to the instant invention was employed in hydroalkylation runs using benzene as the feed in the following manner. A tubular reactor was charged with 15 ml (11.4 grams) of the above catalyst and the catalyst reduced at 150° C. for 15 minutes under 3,450 kPa (500 psig) hydrogen at a hydrogen flow rate of 0.32 liter per minute. Benzene was then charged to the reactor at a rate of about 100 ml per hour. Effluent from the hydroalkylation reaction zone was collected periodically and analyzed by gas-liquid phase chromatography. Other conditions employed in this run and the results obtained are shown below in Table I.

Table I

| Run No. | Temp. °C | LHSV | Benzene Conv. % | Selectivity, % | | | | | Ratio CHB/CH |
|---|---|---|---|---|---|---|---|---|---|
| | | | | CH[a] | CHB[b] | D[c] | E[d] | H[e] | |
| 1 | 155 | 10 | 4.9 | 96 | 4 | — | — | — | 0.04 |

Table I-continued

| Run No. | Temp. °C | LHSV | Benzene Conv. % | Selectivity, % | | | | | Ratio CHB/CH |
| | | | | CH[a] | CHB[b] | D[c] | E[d] | H[e] | |
|---|---|---|---|---|---|---|---|---|---|
| 2 | 235 | 15 | 9.5 | 94 | 6 | — | — | — | 0.07 |

(a) CH = cyclohexane
(b) CHB = cyclohexylbenzene
(c) D = $C_{12}H_{22}$ hydrocarbons
(d) E = methylcyclopentylbenzenes
(e) H = heavies It can be seen from the results of Table I that the above-described catalyst had a low selectivity for the production of cyclohexylbenzene and produced primarily cyclohexane in the hydroalkylation reaction zone.

EXAMPLE II (Runs 3-24)

A number of compositions were prepared according to the instant invention. The support materials for these catalysts were prepared by treating 200 grams of the Type X crystalline zeolite utilized in Example I above with mixtures of ammonium chloride and rare earth chlorides of varying weight ratios in order to exchange the sodium content of the crystalline zeolite for the ammonium and rare earth cations. The rare earth chlorides utilized in the above-described runs was a commercially available mixture obtained from the American Potash Corporation and having the following composition: $MCl_3.6H_2O$ wherein M = lanthanum 23 percent; cerium 43.5 percent; praseodymium 5.4 percent; neodymium 17.9 percent; samarium 1.9 percent; gadolinium 0.6 percent; and others 0.2 percent. The cationic exchange process utilizing a mixture of ammonium chloride and the rare earth chlorides employed 4 liters of water to dissolve the ammonium and rare earth chlorides. The aqueous solution was pumped over the support material held at a temperature of about 90° to 105° C. at a liquid hourly space velocity of 0.25. In each catalyst support preparation run, the support material after the cationic exchange step was washed thoroughly with water, dried and then calcined substantially according to the conditions given in Example I above. The support materials were then impregnated with mixtures of ruthenium chloride and nickel chloride also in the same manner as employed in Example I in order to provide final catalyst composites having 0.10 weight percent ruthenium and 0.10 weight percent nickel. Other details and data characterizing the catalysts are presented below in Table IIA.

Table IIA

| Catalyst No. | $NH_4Cl$[a] % | RECl[b] % | Na Content[c] % | RE Content[d] % |
|---|---|---|---|---|
| 2 | 5 | 2.5 | 1.09 | 13[g] |
| 3 | 2 | 5 | 0.91 | 16[g] |
| 4[f] | 2 | 5 | 0.91 | 16[g] |
| 5 | 5 | 5 | 0.82 | 16[g] |
| 6 | 10 | 5 | 0.65 | 16.37 |
| 7[e] | 5 | 2.5 | 1.09 | 13[g] |

(a) Wt. % $NH_4Cl$ in ion exchange solution.
(b) Wt. % rare earth chlorides (RECl) in ion exchange solution.
(c) Sodium content of zeolite after ion exchange and calcination.
(d) Rare earth content of zeolite after ion exchange and calcination.
(e) Nickel bromide was used instead of nickel chloride in the impregnation step.
(f) Catalyst was heated for 2 hours at 550° F. in air after impregnation.
(g) Estimated values.

The above-described catalysts were employed for the hydroalkylation of benzene to cyclohexylbenzene in a reactor essentially the same as that employed in Example I. Again, samples of the effluent from the reaction zone were collected and analyzed by gas-liquid phase chromatography. Aside from the desired product cyclohexylbenzene and unreacted benzene, the principal components as by-products in the reaction zone effluent are cyclohexane, bicyclohexyl, methylcyclopentylbenzene and heavier materials. The results obtained in the hydroalkylation runs as well as the reaction conditions employed are presented below in Table IIB.

Table IIB

| Run No. | Catalyst No. | Temp., °C | LHSV | Benzene Conv., % | Selectivity, %[a] | | | | | Ratio CHB/CH |
| | | | | | CH | CHB | D | E | H | |
|---|---|---|---|---|---|---|---|---|---|---|
| 3 | 2 | 190 | 17 | 8.3 | 14 | 83 | —[b] | 2 | — | 5.8 |
| 4 | 2 | 172 | 17 | 5.6 | 11 | 88 | — | 2 | — | 7.6 |
| 5 | 2 | 188 | 17 | 5.2 | 8 | 90 | — | 3 | — | 11.0 |
| 6 | 2 | 212 | 17 | 5.9 | 7 | 82 | — | 3 | 8 | 12.0 |
| 7 | 2 | 175 | 20 | 7.9 | 14 | 76 | 0.5 | 1 | 8 | 5.4 |
| 8 | 2 | 165 | 14 | 9.2 | 15 | 74 | 0.5 | 1 | 9 | 4.8 |
| 9 | 3 | 158 | 17 | 9.6 | 34 | 55 | 1 | 1 | 9 | 1.6 |
| 10 | 3 | 172 | 17 | 11.1 | 34 | 58 | 0.5 | 1 | 7 | 1.7 |
| 11 | 3 | 185 | 19 | 11.1 | 32 | 61 | — | 1 | 5 | 1.9 |
| 12 | 4 | 152 | 16 | 10.0 | 23 | 68 | 1 | 1 | 8 | 3.0 |
| 13 | 4 | 167 | 16 | 7.4 | 39 | 57 | 3 | 1 | — | 1.4 |
| 14 | 4 | 186 | 15 | 7.4 | 41 | 57 | 1 | 2 | — | 1.4 |
| 15 | 5 | 162 | 20 | 11.8 | 17 | 74 | 0.5 | 1 | 8 | 4.4 |
| 16 | 5 | 174 | 20 | 7.7 | 16 | 71 | 1 | 1 | 12 | 4.6 |
| 17 | 5 | 175 | 20 | 6.0 | 13 | 75 | 1 | 2 | 10 | 5.5 |
| 18 | 6 | 150 | 15 | 13.7 | 12 | 78 | — | 2 | 8 | 6.5 |
| 19 | 6 | 175 | 15 | 9.9 | 9 | 80 | — | 4 | 8 | 8.8 |
| 20 | 6 | 150 | 15 | 7.0 | 13 | 77 | — | 1 | 8 | 5.8 |
| 21 | 6 | 150 | 18 | 7.7 | 13 | 75 | 0.5 | 3 | 8 | 5.8 |
| 22 | 6 | 160 | 17 | 9.5 | 12 | 76 | — | 2 | 10 | 6.5 |
| 23 | 7 | 155 | 11 | 5.5 | 9 | 89 | — | 1 | — | 9.8 |
| 24 | 7 | 170 | 6.7 | 8.3 | 8 | 80 | — | 2 | 11 | 9.4 |

(a) See footnotes for Table I.
(b) A dash (—) indicates not detected or less than 0.5 percent in terms of selectivity.

As can be seen from the results shown in Table IIB, the catalysts of the instant invention provide a high selectivity to cyclohexylbenzene in the hydroalkylation of benzene. Furthermore, the conversion of benzene in the reaction zone is reasonably good with the catalysts of the instant invention. It is recognized, of course, that unreacted benzene can be recycled conveniently to the reaction zone.

EXAMPLE III (Runs 25-27)

Another catalyst (No. 8) was prepared according to the instant invention in essentially the same manner as those of Example II; however, in this case the ruthenium content on the final catalyst composite was 0.05 weight percent and the nickel content was 0.2 weight percent. The catalyst support for the instant catalyst was the same as that employed in the preparation of catalyst No. 2 in Example II and thus contained about 13 percent by weight rare earth metals. The results obtained with the instant catalyst in benzene hydroalkylation runs and the conditions employed in said runs are presented below in Table III.

Table III

| Run No. | Temp., °C. | LHSV | Benzene Conv., % | Selectivity, %[a] | | | | | Ratio CHB CH |
|---|---|---|---|---|---|---|---|---|---|
| | | | | CH | CHB | D | E | H | |
| 25 | 178 | 19 | 7.3 | 13 | 84 | 1 | 1 | 2 | 6.3 |
| 26 | 185 | 20 | 7.9 | 10 | 76 | 0.5 | 2 | 12 | 7.5 |
| 27 | 154 | 6.7 | 12.1 | 13 | 73 | 1 | 1 | 12 | 5.5 |

(a) See footnotes for Table I.

The results shown in Table III indicate that the above catalyst shows good selectivity to cyclohexylbenzene at reasonably good benzene conversion levels.

EXAMPLE IV (Runs 28-31)

In a manner similar to that employed in the catalyst preparation runs of Example II, a zeolite support material of Type Y (SK-40, Linde Division, Union Carbide Corp.) of 10-14 mesh size was treated with 200 grams of ammonium chloride and 100 grams of the above-described rare earth chloride mixture in 4 liters of water. One hundred seventeen grams of the crystalline zeolite was cation exchanged under the conditions described in Example II. After water washing, drying and then calcining the support, there was obtained 113.4 grams of the cation exchanged crystalline Type Y zeolite. Analysis indicated that the sodium content of the exchanged zeolite was 1.61 weight percent. The rare earth metals content was about 12 percent by weight.

Twenty-five grams of the above-described support material was impregnated with a solution of 0.0621 gram of ruthenium trichloride and 0.1007 grams of nickel chloride hexahydrate in 80 ml of absolute ethanol. The ethanol was removed under reduced pressure on a rotary evaporator and the catalyst (No. 9) then utilized in the hydroalkylation of benzene under the conditions shown in Table IV below. The ruthenium content was 0.10 percent by weight and the nickel content was 0.10 percent by weight for said catalyst.

Table IV

| Run No. | Temp., °C | LHSV | Benzene Conv., % | Selectivity, %[a] | | | | | Ratio CHB CH |
|---|---|---|---|---|---|---|---|---|---|
| | | | | CH | CHB | D | E | H | |
| 28 | 165 | 12 | 10.1 | 14 | 77 | — | 1 | 8 | 5.6 |
| 29 | 140 | 6 | 8.1 | 20 | 73 | — | 1 | 6 | 3.8 |
| 30 | 160 | 9 | 14.3 | 20 | 68 | — | 1 | 10 | 3.5 |
| 31 | 185 | 15 | 10.8 | 21 | 70 | 0.5 | 1 | 8 | 3.3 |

(a) See footnotes for Table I.

The results shown in Table IV indicate the suitability of a Type Y crystalline zeolite as a support material when exchanged with a mixture of rare earth chlorides and ammonium chloride and then impregnated with a mixture of ruthenium and nickel chlorides to thereby produce a hydroalkylation catalyst according to the instant invention.

EXAMPLE V

As additional control runs, catalysts were prepared whereby a support material which was an acid activated montmorillonite clay (Filtrol Grade 49) of 10-14 mesh size was cationic exchanged with a mixture of ammonium chloride and rare earth chlorides in a manner similar to that employed for the catalysts of Example II. In said catalyst support preparation, a mixture of 185 grams of Filtrol Grade 49 of size 10-14 mesh was heated at 282°-296° C. (540°-565° F.) for 2 hours, then treated with water and charged to the exchange reactor. A solution of 125 grams of ammonium chloride and 62.5 grams of the rare earth chlorides utilized in Example II in 2500 ml of water was then pumped over the clay support at a temperature of 95°-100° C. The exchanged clay was cooled then filtered and washed six times with 350 ml portions of water. The support was allowed to dry in the air and there was obtained 234 grams of the treated clay support. One-half of the treated clay was heated at 304°-321° C. (580°-610° F.) for 2 hours and there was obtained therefrom 77 grams of support material. Both the heated and unheated support material were utilized in the preparation of catalysts by impregnation of said supports with absolute ethanol solutions of ruthenium chloride and nickel chloride hexahydrate in a manner previously described. After evaporation of the absolute ethanol under reduced pressure in a rotary evaporator, the ruthenium and nickel contents of the final catalyst composites were in each case 0.10 percent ruthenium and 0.10 percent nickel (No. 10, No. 11). Both catalysts were then tested as benzene hydroalkylation catalysts in the reaction system described in the earlier examples. Both catalysts were found to be extremely active hydrogenation catalysts producing essentially cyclohexane and very small amounts of cyclohexylbenzene in the hydroalkylation reaction zone. Temperatures from about 160°-205° C. were employed and the values for liquid hourly space velocity ranged from about 7 to 23 in the tests with these catalysts. These results demonstrate that the catalysts described herein were not effective for hydroalkylation of benzene to produce cyclohexylbenzene in comparison with the catalysts of the instant invention which were described above.

EXAMPLE VI (Runs 32-36)

Another series of runs was carried out in a manner similar to the runs of Example I to show the necessity for all the components of the catalyst system. The reaction pressure was 3,450 kPa (500 psig) hydrogen and the hydrogen flow rate was 0.32 liter per minute. Table V below shows the various other reaction parameters employed.

Table V

Catalysts From Mole Sieves With Ru and Ni

| Run No. | % NH$_4$Cl[a] | % RECl's[b] | wt.[c] % Ni | wt.[c] % Ru | wt.[c] % RE | Catalyst No. | Rx Temp., °C. | LHSV | Benzene Conversion | CHB Select., % | Ratio CHB/CH |
|---|---|---|---|---|---|---|---|---|---|---|---|
| 32 | 5.0 | — | 0.1 | 0.1 | — | 13 | 235 | 15 | 9.5 | 6.5 | 0.07 |
| 33 | 5.0 | 5.0 | 0.1 | 0.1 | 16[d] | 14 | 162 | 20 | 11.8 | 73.8 | 4.4 |
| 34 | 5.0 | 5.0 | — | 0.1 | 16[d] | 15 | 161 | 20 | 12.0 | 62.9 | 2.5 |
| 35 | 5.0 | 5.0 | 0.1 | — | 16[d] | 16 | 162 | 20 | none | — | — |
| 36 | 5.0 | 5.0 | 0.1 | — | 16[d] | 16 | 188 | 20 | none | — | — |

(a) wt. % NH$_4$Cl in ion exchange solution
(b) wt. % rare earth chlorides (RECl) in ion exchange solution
(c) wt. % Ni and Ru in the catalyst based on total weight of the catalyst
(d) estimated values Run 32 was carried out without the use of rare earths. Run 32 had a CHB selectivity of only 6.5 percent and a CHB/CH ratio of only 0.07 as compared to Run 33 which was carried out in accordance with the invention in which the CHB selectivity was 73.8 percent and the CHB/CH ratio was 4.4. Control Runs 35 and 36 which were carried out without employing Ru provided no benzene conversion. Control Run 34 which was carried out without employing Ni provided a 14.8 percent decrease in CHB selectivity as compared to Run 33 and a CHB/CH ratio of 2.5 as compared to 4.4 for Run 33.

EXAMPLE VII (Runs 37-42)

In another continuous hydroalkylation reaction system, the reactor was charged with 7.5 ml (6.48 grams) of a catalyst of the instant invention. Said catalyst (No. 16) was prepared by the same procedure given for catalyst No. 6 of Example II above. The final catalyst composite thus contained 0.1 weight percent ruthenium and 0.1 weight percent nickel and about 16 percent by weight rare earth metals. The reactor was closed and leak tested with nitrogen at 3800 kPa (550 psig). The reactor was vented and then purged three times with hydrogen. Benzene hydroalkylation was carried out over the above catalyst at a temperature of 150° C. and a hydrogen feed rate of 0.50 moles per hour at 3445 kPa (500 psig) and 150° C. (11.3 liters per hour at standard conditions) and at a benzene feed rate of 78 ml per hour (10.4 LHSV). The effluent from the reaction zone was sampled at periodic intervals and the sample analyzed by gas-liquid phase chromatography. As indicated in Table VI below, the hydroalkylation reaction was carried out over a period of days. The results obtained during this extended run are shown in Table VI. The run was continued for several more days while the temperature was increased to 160° then 170° C. Also, 5 ppm of CCL$_4$ was added to the feed during a portion of this latter period of the run. Neither the temperature increase nor the CCL$_4$ additive appeared to halt the gradual decline in catalyst activity which is evident in the results shown in Table VI. However, the results in Table VI demonstrate that a catalyst of the instant invention was suitable for the hydroalkylation of benzene to cyclohexylbenzene in good selectivity and at reasonably good conversion levels for a period of several days.

Table VI

| Run No. | Time, Days | GLC, Area % A[a] | Benzene | U[b] | CHB | Ratio CHB/A[c] |
|---|---|---|---|---|---|---|
| 37 | 1 | 3.01 | 84.38 | 0.24 | 12.36 | 4.11 |
| 38 | 2 | 3.13 | 83.78 | 0.24 | 12.85 | 4.10 |
| 39 | 3 | 3.09 | 83.95 | 0.28 | 12.68 | 4.10 |
| 40 | 4 | 2.38 | 85.70 | 0.2 | 11.28 | 3.99 |
| 41 | 5 | 2.08 | 89.23 | 0.2 | 8.49 | 4.09 |
| 42 | 6 | 1.75 | 90.89 | 0.15 | 7.21 | 4.13 |

[a] Cyclohexane (CH) and methylcyclopentylbenzene.
[b] C$_{12}$H$_{22}$'s and methylcyclopentylbenzenes.
[c] GLC area percent ratio is an indicator of selectivity for CHB production. The higher the ratio the higher the selectivity to CHB production.

What is claimed is:

1. A process for producing monocycloalkyl aromatic hydrocarbons and substituted monocycloalkyl aromatic hydrocarbons which comprises:

contacting a monocyclic aromatic hydrocarbon or an alkyl substituted monocyclic aromatic hydrocarbon under hydroalkylation conditions and in the presence of hydrogen with a catalyst consisting essentially of at least one ruthenium compound and at least one nickel compound supported on a calcined, acidic, rare earth-treated crystalline zeolite selected from the group consisting of Type X and Type Y zeolites.

2. The process of claim 1 wherein the ruthenium content and nickel content each range from about 0.01 to about 1 percent by weight.

3. The process of claim 1 wherein the ruthenium content and nickel content each range from about 0.05 to about 0.25 percent by weight.

4. The process of claim 1 wherein the nickel to ruthenium weight ratio ranges from about 1:1 to about 2:1.

5. The process of claim 1;
    wherein the rare earth metal compound is selected from the group consisting of nitrates, bromides, acetates, chlorides, iodides, sulfates and mixtures thereof;
    wherein the rare earth metal is selected from the group consisting of cerium, lanthanum, praseodymium, neodymium, samarium, europium, gadolinium, terbium, dysprosium, holmium, erbium, thulium, ytterbium, and lutetium and mixtures thereof; and
    the ruthenium and nickel compounds are selected from the group consisting of chlorides, nitrates and acetates.

6. The process of claim 1 wherein the crystalline zeolite is the alkali metal form with the alkali metal content of the calcined, acidic, rare earth-treated crystalline zeolite ranging from about 0.01 to about 2 percent by weight; and
    wherein the rare earth content of the calcined, acidic, rare earth-treated crystalline zeolite ranges from about 2 to about 25 percent by weight.

7. The process of claim 1 wherein the crystalline zeolite is the alkali metal form with the alkali metal content of the calcined, acidic, rare earth-treated crystalline zeolite ranging from about 0.5 to about 1 percent by weight; and wherein the rare earth content of the calcined, acidic, rare earth-treated crystalline zeolite ranges from about 5 to about 20 percent by weight.

8. The process of claim 1 wherein the monocyclic aromatic hydrocarbon is contacted with said catalyst at a liquid hourly space velocity ranging from about 1 to about 100, a hydrogen pressure ranging from about 690 to about 13,800 kilopascals (100 to 2000 psig), a hydrogen feed rate ranging from about 0.1 to about 10 moles of hydrogen per mole of monocyclic aromatic hydrocarbon per hour, and a temperature ranging from about 100° to about 250° C.

9. The process of claim 1 wherein the monocyclic aromatic hydrocarbon is contacted with said catalyst at a liquid hourly space velocity ranging from about 5 to about 25, a hydrogen pressure ranging from about 1380 to about 6900 kilopascals (200 to 1000 psig), a hydrogen feed rate ranging from about 0.2 to about 1 mole of hydrogen per mole of monocyclic aromatic hydrocarbon per hour, and a temperature ranging from about 140° to about 200° C.

10. The process of claim 1 wherein the catalyst is contacted with hydrogen gas prior to contacting said monocyclic aromatic hydrocarbon.

11. The process of claim 9 wherein the hydrogen gas pressure ranges from about 690 to about 13,800 kilopascals (100 to 2000 psig).

12. The process of claim 1 wherein
the ruthenium compound is ruthenium trichloride, the nickel compound is nickel chloride hexahydrate, and the rare earth metal compound used to treat the crystalline zeolite is a mixture of the chlorides of at least lanthanum, cerium, praseodymium, neodymium, samarium and gadolinium.

* * * * *